(12) United States Patent
Ma et al.

(10) Patent No.: US 11,078,138 B2
(45) Date of Patent: Aug. 3, 2021

(54) SUGAR HYDROGENOLYSIS WITH MOLYBDENUM CO-CATALYST SELECTIVE FOR PRODUCING GLYCOLS

(71) Applicant: Archer Daniels Midland Company, Decatur, IL (US)

(72) Inventors: Chi Cheng Ma, Champaign, IL (US); James Brazdil, Glen Ellyn, IL (US)

(73) Assignee: ARCHER DANIELS MIDLAND COMPANY, Decatur, IL (US)

( * ) Notice: Subject to any disclaimer, the term of this patent is extended or adjusted under 35 U.S.C. 154(b) by 0 days.

(21) Appl. No.: 16/968,154

(22) PCT Filed: Jan. 29, 2019

(86) PCT No.: PCT/US2019/015626
§ 371 (c)(1),
(2) Date: Aug. 6, 2020

(87) PCT Pub. No.: WO2019/156854
PCT Pub. Date: Aug. 15, 2019

(65) Prior Publication Data
US 2020/0361839 A1 Nov. 19, 2020

Related U.S. Application Data

(60) Provisional application No. 62/628,644, filed on Feb. 9, 2018.

(51) Int. Cl.
| | | |
|---|---|---|
| *C07C 29/141* | (2006.01) | |
| *B01J 21/18* | (2006.01) | |
| *B01J 23/30* | (2006.01) | |
| *B01J 23/652* | (2006.01) | |

(52) U.S. Cl.
CPC ............ *C07C 29/141* (2013.01); *B01J 21/18* (2013.01); *B01J 23/30* (2013.01); *B01J 23/6525* (2013.01)

(58) Field of Classification Search
CPC ..... C07C 29/60; C07C 31/205; C07C 29/132; C07C 31/202
See application file for complete search history.

(56) References Cited

U.S. PATENT DOCUMENTS

| | | |
|---|---|---|
| 5,543,379 A | 8/1996 | Gubitosa et al. |
| 6,291,725 B1 | 9/2001 | Chopade et al. |
| 2010/0256424 A1 | 10/2010 | Zhang et al. |
| 2017/0362146 A1 | 12/2017 | Van Der Waal et al. |
| 2019/0194100 A1* | 6/2019 | Wang ............... C07C 29/14 |

FOREIGN PATENT DOCUMENTS

WO  WO 2017-011615   1/2017

* cited by examiner

*Primary Examiner* — Jafar F Parsa
(74) *Attorney, Agent, or Firm* — William B. Miller

(57) ABSTRACT

A hydrogenolysis process is disclosed for directly converting a sugar feed comprised of a high fructose feedstock, a high sucrose feedstock, or a combination of these to a mixed lower polyols product including both propylene glycol and ethylene glycol. The process provides greater propylene glycol selectivity than ethylene glycol selectivity such that the propylene glycol is present to a greater extent than the ethylene glycol in the mixed lower polyols product. The sugar feed and a source of hydrogen are supplied to a reaction vessel and reacted in the presence of a hydrogenolysis catalyst comprising molybdenum (Mo) and ruthenium (Ru).

18 Claims, No Drawings

SUGAR HYDROGENOLYSIS WITH MOLYBDENUM CO-CATALYST SELECTIVE FOR PRODUCING GLYCOLS

This application is a national stage entry of International Application No. PCT/US19/15626, filed Jan. 29, 2019, which itself claims priority to U.S. Provisional Patent Application No. 62/628644, filed Feb. 9, 2018, the contents of each are incorporated herein by reference.

TECHNICAL FIELD

The present invention relates generally to catalysts, and more particularly, to co-catalysts having an enhanced ability to produce glycols from reaction of sugars and hydrogen.

BACKGROUND ART

Conventional methods of producing biobased glycols involve reacting pure hydrogen with sugars (fructose and glucose) and sugar alcohols over hydrogenation and hydrogenolysis catalytic materials. Hydrogenolysis is a chemical reaction wherein a carbon-carbon or carbon-heteroatom single bond is cleaved and undergoes lysis (breakdown) by hydrogen. Hydrogenation is a reaction wherein hydrogen is added to a molecule, without cleaving bonds.

U.S. Pat. No. 4,496,780 discloses the hydrocracking of carbohydrate polyols using a heterogeneous catalyst of a Group VIII metal such as ruthenium composited on a support and an alkaline earth metal oxide. The process requires a temperature of 150° to 250° C. and a pressure of 500 to 5,000 psig.

U.S. Pat. No. 4,476,331 discloses hydrogenolysis of hydrogenated sugars to lower polyhydric alcohols using a supported, sulfided $RuCl_3$ catalyst and a base, at a temperature of 150° to 300° C. and a hydrocarbon pressure of 500 to 5,000 psig.

U.S. Pat. No. 4,401,823 describes the hydrogenolysis of polyhydroxylated compounds, such as sugars and alcohols, in the presence a catalyst impregnated with a metal, for example, transition metals such as chromium, molybdenum, tungsten, rhenium, manganese, copper, cadmium and the Group VIII metals of the Periodic Table including iron, cobalt, nickel, as well as the noble metals such as platinum, palladium, rhodium, ruthenium, iridium and osmium to produce alcohols, acids, ketones, and ethers, at 175° to 250° C. and 10 to 2,000 psi.

Various other approaches using catalysts have been disclosed for producing polyols and other compounds from biomass-derived oxygenated hydrocarbons, such as sugars, sugar alcohols, saccharides and the like.

For example, U.S. Pat. No. 8,710,281 describes methods for producing polyols, ketones, carboxylic acids, aldehydes and alcohols from biomass-derived oxygenated hydrocarbons, such as sugars, sugar alcohols, saccharides and the like, using catalysts containing platinum, ruthenium and tin. The disclosed methods involve aqueous phase reforming (APR) using an APR catalyst, followed by hydrodeoxygenation. The APR catalyst is described as including a support and at least one Group VIIIB metal, such as Ru among others. The patent also states that the APR catalyst may also include at least one additional material from Group VIIIB, Group VIIB, Group VIB, Group VB, Group IVB, Group IIB, Group IB, Group IVA, Group VA metals and lanthanoids, such as Mo among others. Similarly, U.S. Pat. No. 7,767,867 describes APR and hydrodeoxygenation methods for generating propylene glycol, ethylene glycol and other compounds from biomass using hydrogen produced from the biomass.

U.S. Pat. No. 9,440,897 describes a process for the preparation of monoethylene glycol from sucrose comprising the steps of: i) hydrolyzing sucrose to form a reaction product stream comprising glucose and fructose; ii) separating the reaction product stream comprising glucose and fructose into a fructose or fructose derivative rich stream and a glucose rich stream; and iii) contacting the glucose rich stream with hydrogen in a reactor in the presence of a solvent and a catalyst system with catalytic hydrogenation abilities to produce a product stream comprising monoethylene glycol with low monopropylene glycol co-production.

WO 2017/055285 describes a process for the production of glycols comprising the step of adding to a reactor vessel a saccharide-containing feedstock, a solvent, hydrogen, a retro-aldol catalyst composition and a catalyst precursor and maintaining the reactor vessel at a temperature and a pressure, wherein the catalyst precursor comprises one or more cations selected from groups 8, 9, 10 and 11 of the periodic table, and wherein the catalyst precursor is reduced in the presence of hydrogen in the reactor vessel into an unsupported hydrogenation catalyst.

WO 2017/055289 describes a process for the preparation of glycols from a saccharide-containing feedstock comprising the steps of: (a) preparing a reaction mixture in a reactor vessel comprising the saccharide-containing feedstock, a solvent, a catalyst component with retro-aldol catalytic capabilities and a first hydrogenation catalyst comprising an element selected from groups 8, 9 and 10 of the periodic table; (b) supplying hydrogen gas to the reaction mixture in the reactor vessel; (c) monitoring the activity of the first hydrogenation catalyst; (d) preparing a second hydrogenation catalyst by contacting in a reactor a catalyst precursor comprising one or more elements selected from chromium and groups 8, 9, 10 and 11 of the periodic table with hydrazine to convert the catalyst precursor into the second hydrogenation catalyst; (e) when the hydrogenation activity declines, supplying the second hydrogenation catalyst to the reactor vessel to supplement the declined hydrogenation activity in the reactor vessel.

WO2017/055281 describes a process for the preparation of an unsupported hydrogenation catalyst wherein a catalyst precursor comprising one or more cations selected from a group consisting of chromium and groups 8, 9, 10 and 11 of the periodic table is contacted in a reactor with hydrazine to convert the catalyst precursor into the unsupported hydrogenation catalyst.

Traditionally, to convert sugar or biomass to propylene glycol (1,2-propanediol or PG) and ethylene glycol ("EG") includes a multi-step process, including (1) hydrolyzing biomass with acid, (2) sugar hydrogenation with catalyst to produce sugar alcohols, and (3) Sugar alcohols hydrogenolysis with catalyst to make PG and EG.

Propylene glycol can be produced by the catalytic hydrogenolysis of sugar alcohols. Commercially, propylene glycol is produced from glycerol. The hydrogenolysis reaction is effectuated by catalysts such as those described in US Patent Application Publication 2009/0088317. The hydrogenolysis reaction used to create propylene glycol results in the production of side products such as ethylene glycol, 2,3-butanediol, 1,2-butanediol, butanediol, 1,4-butanediol, 2,3-pentanediol, and 2,4-pentanediol. However, these diols and the ethylene glycol are difficult to separate from the propylene glycol, and one isomer of the 2,3-pentanediol cannot be economically separated from propylene glycol by, distillation. While it is possible to reduce the production of such diols by varying the hydrogenolysis reactions, such variances may reduce the overall productivity of the propylene glycol process.

Methods have been developed to isolate or purify the propylene glycol from these diols and/or the ethylene glycol. U.S. Pat. No. 8,143,458, assigned to Archer-Daniels-Midland Company, discloses processes for producing propylene glycol and separating the unwanted diols from the propylene glycol. While such processes are able to effectively separate the diols from the propylene glycol, such processes are time consuming and expensive.

SUMMARY OF THE INVENTION

In each of its various embodiments, the present invention fulfills the need for more efficient production of glycols, in particular, including propylene glycol, from sugars. In an aspect, a process is disclosed for directly converting a sugar feed comprised of a high fructose feedstock, a high sucrose feedstock, or a combination of these to a mixed lower polyols product including both propylene glycol and ethylene glycol. In an aspect, the process provides greater propylene glycol selectivity than ethylene glycol selectivity such that the propylene glycol is present to a greater extent than the ethylene glycol in the mixed lower polyols product. In an aspect, the sugar feed and a source of hydrogen are supplied to a reaction vessel and reacted in the presence of a hydrogenolysis catalyst comprising molybdenum (Mo) and ruthenium (Ru) such that the propylene glycol is formed.

In an aspect, a co-catalyst is disclosed that may be used in a one-step reaction between a sugar and hydrogen where the co-catalyst provides an enhanced selectivity to propylene glycol and ethylene glycol at a greater conversion, with a reduced production of higher polyols. In an aspect, the invention results in a greater productivity of propylene glycol and ethylene glycol in the resulting product mixture, and reduced costs in separating propylene glycol and ethylene glycol from the product mixture.

In an aspect, a co-catalyst is disclosed that may be used in a one-step reaction between a sugar and hydrogen where the co-catalyst provides an enhanced selectivity to propylene glycol at a greater conversion, with a reduced production of ethylene glycol as well as of higher polyols. In an aspect, the invention results in a greater productivity of propylene glycol in the resulting product mixture, and reduced costs in separating pure propylene glycol from the product mixture.

In an aspect, a co-catalyst for the one-step reaction comprises a bimetallic or multi-metallic catalyst comprising molybdenum (Mo) and ruthenium (Ru).

In an aspect, a process for producing propylene glycol comprises placing a sugar feedstock in contact with a co-catalyst comprising Mo and Ru such that a high selectivity of propylene glycol and ethylene glycol is achieved.

In an aspect, a co-catalyst for treatment of a sugar feedstock with hydrogen to produce propylene glycol and ethylene glycol comprises support material and catalytic metal components comprising Mo and Ru.

DETAILED DESCRIPTION OF EMBODIMENTS

The term "comprising" as used in this specification and claims means "consisting at least in part of". When interpreting statements in this specification, and claims which include the term "comprising", it is to be understood that other features that are additional to the features prefaced by this term in each statement or claim may also be present. Related terms such as "comprise" and "comprised" are to be interpreted in similar manner.

Further, in the present application, including the claims, other than in the operating examples or where otherwise indicated, all numbers expressing quantities or characteristics are to be understood as being modified in all instances by the term "about". Unless indicated to the contrary, any numerical parameters set forth in the following description may vary depending on the desired properties in the compositions and methods according to the present disclosure. At the very least, and not as an attempt to limit the application of the doctrine of equivalents to the scope of the claims, each numerical parameter described in the present description should at least be construed in light of the number of reported significant digits and by applying ordinary rounding techniques.

Any patent, publication, or other disclosure material, in whole or in part, that s said to be incorporated by reference herein is incorporated herein only to the extent that the incorporated material does not conflict with existing definitions, statements, or other disclosure material set forth in this disclosure. As such, the disclosure set forth herein supersedes any conflicting material incorporated herein by reference.

In an embodiment, the present invention discloses co-catalysts for the conversion of a sugar, such as fructose, dextrose and/or sucrose, to produce propylene glycol and ethylene glycol in a one-step hydrogenolysis process.

In another embodiment, the present invention discloses a process for conversion of a sugar with an improved selectivity for propylene glycol and ethylene glycol, while reducing the formation of higher polyols.

In an embodiment, the present invention discloses co-catalysts for the conversion of a sugar, such as fructose, dextrose and/or sucrose, to produce an enhanced amount of propylene glycol in a one-step hydrogenolysis process.

In another embodiment, the present invention discloses a process for conversion of a sugar with an improved selectivity for propylene glycol over the selectivity of ethylene glycol, while reducing the formation of higher polyols.

In one embodiment, the present invention provides co-catalysts and uses thereof for reaction of sugars which maximize the selectivity of the reaction towards the formation of propylene glycol and ethylene glycol, while minimizing the formation of other polyols. In a further embodiment, the co-catalyst comprises catalyst components including ruthenium (Ru) and molybdenum (Mo). In an embodiment, Ru is present at 3-7% by weight of the hydrogenolysis catalyst. In a more preferred embodiment, Ru is present at about 5% by weight of the hydrogenolysis catalyst. In an embodiment, Mo is present at 0.5 to 10% by weight of the sugar feed. Preferably, Mo is present at 3-10% by weight of the sugar feed. In an embodiment, Mo is present at about 9-10% by weight of the sugar feed.

In one embodiment, the metal catalyst components may be impregnated on a support material in salt form. In other embodiments, the metal catalyst components may be impregnated on a support material in oxide or element form as well.

In another embodiment, reaction conditions are provided such that sugar feedstocks are converted to propylene glycol in one-step. In one embodiment, the reaction conditions of the sugar reaction may be varied to optimize the performance of the co-catalysts of the present invention for the selective formation of propylene glycol. Such optimized conditions are able to produce propylene glycol with little or negligible formation of other polyols that are difficult to separate from the propylene glycol by distillation, for example, with less than about 2% selectivity to the four carbon and higher polyols, preferably with less than about 1% selectivity to such higher polyols, and more preferably less than about 0.5% selectivity to these higher polyols.

In an additional embodiment, a process is provided for hydrogenolysis of a sugar feedstock to propylene glycol comprising placing a sugar feedstock in contact with hydrogen and a co-catalyst of the present invention at a liquid hourly space velocity of 0.2 $hr^{-1}$ to 2 $hr^{-1}$ to minimize the formation of higher polyols in a fixed-bed reactor.

In yet a further embodiment, the process for hydrogenolysis of a sugar feedstock to propylene glycol may be conducted at a reaction temperature of 180° C. to 250° C. in order to minimize the formation of higher polyols. In yet a further embodiment, the reaction temperature may be 200° C. to 220° C.

In one embodiment, the sugar feedstock used in the present invention may be biomass or derived from a biomass source. In an embodiment, the sugar feedstock may be a by-product or waste stream of another process. For example, the sugar feedstock may be a by-product or waste stream of a starch hydrolysis process, or a pulp process, or a combination thereof.

In a further embodiment, the product produced using co-catalysts disclosed herein may comprise a mixture of propylene glycol and ethylene glycol, along with minor amounts of other compounds, such as glycerol. In an embodiment, the process using co-catalysts disclosed herein does not produce butanediols (BDO) in amounts significant enough to be measurable by typical gas chromatography.

In various embodiments, the product of the present invention comprising the propylene glycol may be used in a composition including, but not limited to, a deicer, an antifreeze, a resin, a laundry detergent, a soap, a personal care product, a cosmetic product, a pharmaceutical product, or as a food ingredient in a food or beverage product.

In another embodiment, the biomass or sugar feedstock includes a diluent, such as water, or a non-aqueous solvent. Non-aqueous solvents that may be used include, but are not limited to, methanol, ethanol, ethylene glycol, propylene glycol, n-propanol, and iso-propanol.

In a further embodiment, co-catalysts for the processes disclosed herein may be solid or heterogeneous catalysts. The co-catalysts may be supported on a support material. A preferred support material may be selected from the group consisting of a carbon based support material, activated carbon, zirconium oxide, titanium oxide, niobium oxide, tin oxide, lanthanum oxide, tungsten oxide, silicon carbide, silicon oxycarbide, titanium carbide, titanium oxycarbide, zirconium oxycarbide, tungsten carbide, tungsten oxycarbide, and combination of any thereof.

The co-catalysts are preferably provided with a large surface area support material that prevents degradation under the reaction conditions. In one embodiment, the surface area may be a Brunauer-Emmett-Teller (BET) surface area between 100 to 1200 $m^2$ per gram. These support materials may include, but are not limited to, carbon, alumina, titania, zirconia, silica, or a combination thereof. These support materials can also be prepared in mixed or layered materials such as mixed with co-catalyst materials Mo and Ru. In an embodiment, tungsten (W) may also be included as a co-catalyst.

The temperature used in the reaction may range from 180° C. to 250° C., and the pressure may range from between 600 psi to 2500 psi. The reaction time for the reaction is defined by the term "weight hourly space velocity" (WHSV) which is the weight of reactant per unit weight of catalyst per hour. Alternatively, the term "liquid hourly space velocity" (LHSV) may also be used, referencing a volume of reactant per unit volume of catalyst per hour. In an embodiment, a value for LHSV is between a velocity of 0.2 $hr^{-1}$ to 2 $hr^{-1}$, which can be modified suitably to meet reactor design specifications using techniques well known to those in the art.

Hydrogenolysis of a biomass or sugar feedstock, as described herein, results in a propylene glycol product. According to certain embodiments, the propylene glycol product may comprise a mixture of propylene glycol and smaller amounts of ethylene glycol, glycerol, and other by-products, such as sorbitol.

Propylene glycol produced by the embodiments described herein may be referred to as "bio-based" propylene glycol. Propylene glycol produced as such finds many uses. Some of these include, but are not limited to, use as a solvent for aromatics in the flavor-concentrate industry; a wetting agent for natural gums; an ingredient in the compounding of citrus and other emulsified flavors; a solvent in elixirs and pharmaceutical preparations; a solvent and coupling agent in the formulation of sunscreen lotion shampoos, shaving creams, and other similar products; an emulsifier in cosmetic and pharmaceutical creams; an ingredient for low-temperature heat-transfer fluids, involving indirect food contacts, such as brewing and dairy uses, as well as refrigerated grocery display cases; a humectant, preservative, and stabilizer in semi-moist pet food, bakery goods, food flavorings, and salad dressings; use as a dust suppression agent; solvents and compatibilizers for dyes, resins, and inks used in modern high-speed printing presses; surface lubricant in metal part manufacture; as a raw material for dipropylene glycol phthalate; a plasticizer for polyvinyl chloride (PVC) resins; for use in the natural gas processing industry; and to provide freeze-thaw protection in various wax products to help prevent damaged caused by freezing. Propylene glycol may also be used as the starting material for the synthesis of propylene glycol esters with sorbitol and/or fatty acids. Such uses are not limited or all inclusive and may be readily developed by those skilled in the art.

Various embodiments of the present disclosure relate to a bio-based propylene glycol and ethylene glycol. The products produced by the processes of the present invention produced by the hydrogenolysis of biomass or sugars feedstocks may be differentiated from petroleum derived products, for example, by their carbon isotope ratios using ASTM International Radioisotope Standard Method D 6866. Products produced from the product mixture of the hydrogenolysis product from a biomass or sugar feedstock may have a bio-based carbon isotope ratio ranging from 50% to 100%. As used herein the term "bio-based carbon isotope ratio" includes a composition or a component of a composition having a carbon isotope ratio, as determined, for example, by ASTM International Radioisotope Standard Method D 6866, the disclosure of which is incorporated by reference herein in its entirety, that is indicative of a composition including, in whole or in significant part, of biological products or renewable agricultural materials (including plant, animal and marine materials) or forestry materials (Method ASTM 6866).

The following exemplary, non limiting examples are provided to further describe the embodiments presented herein. Those having ordinary skill in the art will appreciate that variations of these Examples are possible within the scope of the present invention. Aspects of the processes and co-catalysts are described in connection with the following examples. Subscripts for chemical compounds are used interchangeably with non-subscripts. For example, potassium molybdate is identified as $K_2MoO_4$.

Example 1

A feed comprising 20% fructose by weight in water was reacted in a high throughput screening batch reactor. The catalytic reaction conditions were carried out in sealed hydrogenolysis reactors at 220 degrees Celsius, at 8.3 MPa (1200 psi) hydrogen pressure for a 2 hour hold period. Products of the reaction were analyzed by gas chromatography ("GC"), which showed enhanced selectivity for propylene glycol using co-catalysts comprising Mo, in the form of potassium molybdate ($K_2MoO_4$) with 5% by weight Ru on carbon powder (hereafter, simply "5% Ru CP"), as compared to sodium tungstate ($Na_2WO_4$) with 5% Ru CP, and as compared to ammonium metavanadate ($NH_4VO_3$) with 5% Ru CP. Results using various reactor co-catalysts are shown in Tables 1-3 below. As shown in Table 1, the co-catalysts comprising potassium molybdate ($K_2MoO_4$) with 5% Ru CP provides greater propylene glycol yield and greater propylene glycol selectivity compared to sodium tungstate ($Na_2WO_4$) with 5% Ru CP (Table 2), and as compared to ammonium metavanadate ($NH_4VO_3$) with 5% Ru CP (Table 3).

TABLE 1

$K_2MoO_4$ as co-catalyst for fructose hydrogenolysis (with 100% fructose conversion); "$K_2MoO_4$, %" means $K_2MoO_4$% by weight of the fructose feed

| $K_2MoO_4$, % | EG Selectivity, % | EG Yield, % | PG Selectivity, % | PG Yield, % | Glycerol Selectivity, % | Sorbitol Selectivity, % |
| --- | --- | --- | --- | --- | --- | --- |
| 0 | 0 | 0 | 1.15 | 0.97 | 0.34 | 0 |
| 3 | 0.53 | 0.51 | 7.05 | 5.95 | 0 | 0 |
| 4 | 1.48 | 1.43 | 11.92 | 10.07 | 0.49 | 0 |
| 5 | 2.95 | 2.85 | 17.57 | 14.84 | 1.88 | 0 |
| 6 | 3.97 | 3.84 | 22.16 | 18.72 | 2.96 | 0 |
| 7 | 5.35 | 5.18 | 26.29 | 22.21 | 5.98 | 0.2 |
| 8 | 6.59 | 6.38 | 27.61 | 23.33 | 6.64 | 1.16 |
| 9 | 6.47 | 6.26 | 26.83 | 22.67 | 6.22 | 0.3 |
| 10 | 7.48 | 7.24 | 28.37 | 23.97 | 7.24 | 1.41 |

TABLE 2

$Na_2WO_4$ as co-catalyst for fructose hydrogenolysis (with 100% fructose conversion); "$Na_2WO_4$ %" means $Na_2WO_4$% by weight of the fructose feed

| $Na_2WO_4$, % | EG Selectivity, % | EG Yield % | PG Selectivity, % | PG Yield % | Glycerol Selectivity, % | Sorbitol Selectivity, % |
| --- | --- | --- | --- | --- | --- | --- |
| 3 | 5.5 | 5.68 | 14.55 | 12.29 | 2.59 | 0 |
| 4 | 4.67 | 4.83 | 12.28 | 10.37 | 1.37 | 0 |
| 5 | 7.53 | 7.78 | 18.95 | 16.00 | 4.65 | 0 |
| 6 | 5.16 | 5.33 | 13.59 | 11.48 | 1.46 | 0 |
| 7 | 6.11 | 6.31 | 19.41 | 16.39 | 2.64 | 0 |
| 8 | 6.43 | 6.64 | 15.89 | 13.42 | 1.27 | 0.39 |
| 9 | 6.84 | 7.07 | 16.7 | 14.10 | 1.48 | 0.47 |
| 10 | 7.63 | 7.88 | 17.84 | 15.06 | 1.74 | 0.6 |

TABLE 3

$NH_4VO_3$ as co-catalyst for fructose hydrogenolysis (with 100% fructose conversion); "$NH_4VO_3$ %" means $NH_4VO_3$ % by weight of the fructose feed

| $NH_4VO_3$, % | EG Selectivity, % | EG Yield, % | PG Selectivity, % | PG Yield, % | Glycerol Selectivity, % | Sorbitol Selectivity, % |
| --- | --- | --- | --- | --- | --- | --- |
| 0 | 0 | 0 | 1.15 | 0.97 | 0.34 | 0 |
| 5 | 0.48 | 0.50 | 11.17 | 9.43 | 0.5 | 0 |
| 6 | 0.28 | 0.29 | 10.1 | 8.53 | 0.2 | 0 |
| 7 | 0 | 0.00 | 2.31 | 1.95 | 0 | 0 |
| 8 | 0 | 0.00 | 3.14 | 2.65 | 0 | 0 |
| 9 | 0 | 0.00 | 3.23 | 2.73 | 0 | 0 |
| 10 | 0 | 0.00 | 2.64 | 2.23 | 0 | 0 |
| Reference | 0 | 0.00 | 0 | 0.00 | 0 | 0 |
| Blank | 0 | 0.00 | 0 | 0.00 | 0 | 0 |

The Reference in Table 3 is 5% Ni/1% Re on Norit ROX washed.

Example 2

A feed comprising 20% sucrose by weight in water was reacted in a high throughput screening batch reactor. The catalytic reaction conditions were carried out in sealed hydrogenolysis reactors at 220 degrees Celsius, at 8.3 MPa (1200 psi) hydrogen pressure for a 2 hour hold period. Products of the reaction were analyzed by gas chromatography ("GC"), which showed enhanced selectivity for propylene glycol using co-catalysts comprising Mo, in the form of potassium molybdate ($K_2MoO_4$) with 5% Ru CP, as compared to sodium tungstate ($Na_2WO_4$) with 5% Ru CP, and as compared to ammonium metavanadate ($NH_4VO_3$) with 5% Ru CP. Results using various reactor co-catalysts are shown in Tables 4-6 below. As shown in Table 4, the co-catalysts comprising potassium molybdate ($K_2MoO_4$) with 5% by weight Ru CP provides greater propylene glycol yield and greater propylene glycol selectivity compared to sodium tungstate ($Na_2WO_4$) with 5% Ru CP (Table 5), and as compared to ammonium metavanadate ($NH_4VO_3$) with 5% Ru CP (Table 6), without sorbitol detected for the runs shown in Tables 4-6.

TABLE 4

$K_2MoO_4$ as co-catalyst for sucrose hydrogenolysis (with 100% sucrose conversion); "$K_2MoO_4$, %" means $K_2MoO_4$ % by weight of the sucrose feed

| K2MoO4, % | EG Selectivity, % | EG Yield, % | PG Selectivity, % | PG Yield, % | Glycerol Selectivity, % |
|---|---|---|---|---|---|
| 3 | 1.36 | 1.42 | 15.82 | 13.36 | 0.58 |
| 4 | 1.23 | 1.28 | 16.35 | 13.81 | 0.42 |
| 5 | 1.8 | 1.88 | 21.42 | 18.09 | 0.82 |
| 6 | 2.02 | 2.11 | 23.15 | 19.55 | 0.84 |
| 7 | 2.43 | 2.54 | 25.27 | 21.34 | 0.9 |
| 8 | 2.39 | 2.50 | 26.1 | 22.04 | 0.75 |
| 9 | 3.22 | 3.36 | 29.09 | 24.56 | 0.86 |
| 10 | 3.02 | 3.15 | 28.11 | 23.74 | 0.84 |

TABLE 5

$Na_2WO_4$ as co-catalyst for sucrose hydrogenolysis (with 100% sucrose conversion); "$Na_2WO_4$ %" means $Na_2WO_4$ % by weight of the sucrose feed

| Na2WO4, % | EG Selectivity, % | EG Yield, % | PG Selectivity, % | PG Yield, % | Glycerol Selectivity, % |
|---|---|---|---|---|---|
| 3 | 0.82 | 0.86 | 7.24 | 6.11 | 0.35 |
| 4 | 3.04 | 3.18 | 13.1 | 11.06 | 1.75 |
| 5 | 2.98 | 3.11 | 13.26 | 11.20 | 1.5 |
| 6 | 3.17 | 3.31 | 14.34 | 12.11 | 1.42 |
| 7 | 2.12 | 2.21 | 13.33 | 11.26 | 0.76 |
| 8 | 2.47 | 2.58 | 14.37 | 12.13 | 0.69 |
| 9 | 2.66 | 2.78 | 15.63 | 13.20 | 0.55 |
| 10 | 2.74 | 2.86 | 15.36 | 12.97 | 0.58 |

TABLE 6

$Na_2WO_4:K_2MoO_4$ as co-catalyst for sucrose hydrogenolysis (with 100% sucrose conversion); "$Na_2WO_4:K_2MoO_4$ %" means $Na_2WO_4:K_2MoO_4$ % by weight of the sucrose feed

| Na2WO4:K2MoO4, % | EG Selectivity, % | EG Yield, % | PG Selectivity, % | PG Yield, % | Glycerol Selectivity, % |
|---|---|---|---|---|---|
| 5Na2WO4:5K2MoO4 | 1.67 | 1.74 | 18.5 | 15.62 | 0.42 |
| 4Na2WO4:4K2MoO4 | 1.61 | 1.68 | 18.28 | 15.44 | 0.3 |
| 3Na2WO4:2K2MoO4 | 0.65 | 0.68 | 11.3 | 9.54 | 0 |
| 2Na2WO4:3K2MoO4 | 1.1 | 1.15 | 15.02 | 12.68 | 0.17 |
| 6Na2WO4:2K2MoO4 | 1.71 | 1.79 | 18.16 | 15.34 | 0.3 |
| 2Na2WO4:6K2MoO4 | 2.29 | 2.39 | 23.74 | 20.05 | 0.74 |
| Reference | 1.03 | 1.08 | 6.74 | 5.69 | 1.08 |
| Blank | 0 | 0.00 | 0 | 0.00 | 0 |

The Reference in Table 6 is 5% Ru/C with no additive.

Example 3

A feed comprising 20% dextrose by weight in water was reacted in a high throughput screening batch reactor. The catalytic reaction conditions were carried out in sealed hydrogenolysis reactors at 220 degrees Celsius, at 8.3 MPa (1200 psi) hydrogen pressure for a 2 hour hold period. Products of the reaction were analyzed by gas chromatography ("GC"), which showed lower ethylene glycol selectivity with greater selectivity for propylene glycol using co-catalysts comprising Mo, in the form of potassium molybdate ($K_2MoO_4$) with 5% Ru CP, as compared to sodium tungstate ($Na_2WO_4$) with 5% Ru CP (with the exception of $5K_2MoO_4$ versus $5Na_2WO_4$ and $10K_2MoO_4$ versus $10Na_2WO_4$ as to PG selectivity).

The GC results also show lower ethylene glycol selectivity with greater selectivity for propylene glycol using co-catalysts comprising Mo, in the form of potassium molybdate ($K_2MoO_4$) with 5% Ru CP as compared to ammonium metavanadate ($NH_4VO_3$) with 5% Ru CP.

Results using various reactor co-catalysts are shown in Table 7-9 below, with 100% dextrose conversion, and without glycerol detected for the runs shown in Tables 7-9.

TABLE 7

K₂MoO₄ as co-catalyst for dextrose hydrogenolysis (with 100% dextrose conversion); "K₂MoO₄, %" means K₂ MoO₄ % by weight of the dextrose feed

| K₂MoO₄, % | EG Selectivity, % | EG Yield, % | PG Selectivity, % | PG Yield, % | Sorbitol Selectivity, % |
|---|---|---|---|---|---|
| 5 | 3.096 | 3.23 | 14.998 | 12.66 | 0 |
| 6 | 4.462 | 4.66 | 18.294 | 15.45 | 0.361 |
| 7 | 5.116 | 5.34 | 18.945 | 16.00 | 0.882 |
| 8 | 5.316 | 5.55 | 18.581 | 15.69 | 0.685 |
| 9 | 6.042 | 6.31 | 18.961 | 16.01 | 1.362 |
| 10 | 9.484 | 9.91 | 18.291 | 15.45 | 1.111 |
| Blank | 0 | 0.00 | 0 | 0.00 | 0 |
| Reference | 0 | 0.00 | 0 | 0.00 | 0 |

The Reference in Table 7 is 5% Ni/1% Re on Norit ROX washed.

TABLE 8

Na₂WO₄ as co-catalyst for dextrose hydrogenolysis (with 100% dextrose conversion); "Na₂WO₄ %" means Na₂ WO₄ % by weight of the dextrose feed

| Na₂WO₄, % | EG Selectivity, % | EG Yield, % | PG Selectivity, % | PG Yield, % | Sorbitol Selectivity, % |
|---|---|---|---|---|---|
| 3 | 6.8 | 7.10 | 13.94 | 11.77 | 0.544 |
| 4 | 6.81 | 7.11 | 14.61 | 12.34 | 0.688 |
| 5 | 8.78 | 9.17 | 15.45 | 13.05 | 0.896 |
| 6 | 8.3 | 8.67 | 15.67 | 13.23 | 0.794 |
| 7 | 7.84 | 8.19 | 16.2 | 13.68 | 0.736 |
| 8 | 8.93 | 9.33 | 16.54 | 13.97 | 1.014 |
| 9 | 9.08 | 9.48 | 17.01 | 14.36 | 1.235 |
| 10 | 9.8 | 10.24 | 18.29 | 15.44 | 0.604 |

TABLE 9

NH₄VO₃ as co-catalyst for dextrose hydrogenolysis (with 100% dextrose conversion); "NH₄VO₃ %" means NH₄ VO₃ % by weight of the dextrose feed

| NH₄VO₃, % | EG Selectivity, % | EG Yield, % | PG Selectivity, % | PG Yield, % | Sorbitol Selectivity, % |
|---|---|---|---|---|---|
| 5 | 1.236 | 1.29 | 14.049 | 11.86 | 0.305 |
| 6 | 1.084 | 1.13 | 14.22 | 12.01 | 0.255 |
| 7 | 0.663 | 0.69 | 12.563 | 10.61 | 0.205 |
| 8 | 0.3 | 0.31 | 9.883 | 8.35 | 0 |
| 9 | 0.223 | 0.23 | 8.025 | 6.78 | 0 |
| 10 | 0.516 | 0.54 | 10.904 | 9.21 | 0.333 |

Table 7 shows greater selectivity of propylene glycol to ethylene glycol from a high dextrose feedstock using a Ru—Mo co-catalyst. The selectivity of propylene glycol from a high dextrose feedstock as shown in Table 7, however, was not as high as the selectivity of propylene glycol from a high fructose feedstock (as shown in Table 1) or a high sucrose feedstock (as shown in Table 4) using a Ru—Mo co-catalyst for corresponding catalyst percent by weight of the sugar feed. Compare, e.g., PG selectivity 28.37% using K₂MoO₄ 10% as co-catalyst for fructose conversion (Table 1), and PG selectivity 28.11% using K₂MoO₄ 10% for as co-catalyst for sucrose conversion (Table 4), with PG selectivity 18.291% using K₂MoO₄ 10% as co-catalyst for dextrose conversion (Table 7).

Example 4

A feed comprising 20% dextrose by weight in water was reacted in a high throughput screening batch reactor. The catalytic reaction conditions were carried out in sealed hydrogenolysis reactors at 220 degrees Celsius, at 1200 psi hydrogen pressure for a 2 hour hold period. Products of the reaction were analyzed by gas chromatography ("GC").

Raney nickel and Raney nickel in combination with sodium tungstate (Na₂WO₄) were tested at a pH range of 3 to 6. Results are shown in Table 10. A comparison of Table 10 and Table 7 shows that the Ru—Mo co-catalysts provide greater propylene glycol selectivity over the catalysts shown in Table 10, and that changing the pH does not significantly change propylene glycol selectivity for the catalysts shown in Table 10.

TABLE 10

(for Different pH, for comparison)

| Catalyst Code | Dextrose Conversion, % | EG Selectivity, % | PG Selectivity, % |
|---|---|---|---|
| Raney Ni pH 3 | 100.00 | 1.10 | 2.23 |
| 1Na2WO4:Raney Ni pH 3 | 100.00 | 1.89 | 3.12 |
| 2Na2WO4:Raney Ni pH 3 | 100.00 | 3.16 | 3.23 |
| 3Na2WO4:Raney Ni pH 3 | 100.00 | 4.78 | 3.54 |
| 4Na2WO4:Raney Ni pH 3 | 100.00 | 2.91 | 2.44 |
| 5Na2WO4:Raney Ni pH 3 | 100.00 | 3.00 | 2.60 |
| Raney Ni pH 4 | 100.00 | 2.53 | 6.31 |
| Blank | 100.00 | 0.00 | 0.00 |
| 2Na2WO4:Raney Ni pH 4 | 100.00 | 2.77 | 3.50 |
| 3Na2WO4:Raney Ni pH 4 | 100.00 | 2.59 | 2.56 |
| 4Na2WO4:Raney Ni pH 4 | 100.00 | 2.11 | 1.74 |
| 5Na2WO4:Raney Ni pH 4 | 100.00 | 2.93 | 3.70 |
| Raney Ni pH 5 | 100.00 | 1.32 | 2.49 |
| 1Na2WO4:Raney Ni pH 5 | 100.00 | 2.08 | 3.86 |
| Reference | 100.00 | 0.00 | 0.00 |
| 3Na2WO4:Raney Ni pH 5 | 100.00 | 2.31 | 1.97 |
| 4Na2WO4:Raney Ni pH 5 | 100.00 | 2.66 | 4.01 |
| 5Na2WO4:Raney Ni pH 5 | 100.00 | 2.78 | 3.94 |
| Raney Ni pH 6 | 100.00 | 1.45 | 2.77 |
| 1Na2WO4:Raney Ni pH 6 | 100.00 | 2.49 | 2.96 |
| 2Na2WO4:Raney Ni pH 6 | 100.00 | 2.37 | 3.12 |
| 3Na2WO4:Raney Ni pH 6 | 100.00 | 2.65 | 3.69 |
| 4Na2WO4:Raney Ni pH 6 | 100.00 | 2.33 | 3.11 |
| 5Na2WO4:Raney Ni pH 6 | 100.00 | 2.19 | 2.99 |

The Reference for Table 10 is Johnson Matthey A3B00 Sponge Copper Batch 3B0000004.

Example 5

Ru/C and Ru—S/C were tested in a high throughput screening batch reactor. A feed comprising 20% dextrose by weight in water was reacted in a high throughput screening batch reactor. The catalytic reaction conditions were carried out in sealed hydrogenolysis reactors at 220 degrees Celsius, at 8.3 MPa (1200 psi) hydrogen pressure for a 2 hour hold period. Products of the reaction were analyzed by gas chromatography ("GC"). The results are shown in Table 11 (catalyst and pH effects). A comparison of Table 11 and Table 7 shows that the Ru—Mo co-catalysts provide greater propylene glycol selectivity over the catalysts shown in Table 11, and that changing the pH does not significantly change propylene glycol selectivity for the catalysts shown in Table 11.

TABLE 11

| Catalyst Code | Dextrose Conversion, % | EG Selectivity, % | PG Selectivity, % |
|---|---|---|---|
| 5% Ru/C pH 3 | 100.00 | 0.58 | 1.99 |
| 1Na2WO4:5% Ru/C pH 3 | 100.00 | 2.04 | 5.50 |
| Blank | 100.00 | 0.00 | 0.00 |
| 3Na2WO45% Ru/C pH 3 | 100.00 | 3.51 | 7.32 |
| 4Na2WO4:5% Ru/C pH 3 | 100.00 | 3.67 | 7.15 |
| 5Na2WO4:5% Ru/C pH 3 | 100.00 | 3.99 | 8.13 |
| 2% Ru 0.1% S pH 3 | 100.00 | 0.39 | 2.30 |
| 2% Ru 0.1% S pH 3 | 100.00 | 0.88 | 2.26 |
| Reference | 100.00 | 1.35 | 3.44 |
| 3Na2WO4:2% Ru 0.1% S pH 3 | 100.00 | 0.74 | 1.18 |
| 4Na2WO4:2% Ru 0.1% S pH 3 | 100.00 | 1.12 | 1.77 |
| 5Na2WO4:2% Ru 0.1% S pH 3 | 100.00 | 0.98 | 1.31 |
| 5% Ru/C pH 4 | 100.00 | 0.78 | 2.40 |
| 1Na2WO4:5% Ru/C pH 4 | 100.00 | 3.09 | 7.03 |
| 5% Ru/C pH 4 | 100.00 | 3.68 | 7.69 |
| 3Na2WO4:5% Ru/C pH 4 | 100.00 | 4.10 | 8.19 |
| 4Na2WO4:5% Ru/C pH 4 | 100.00 | 4.23 | 8.56 |
| 5Na2WO4:5% Ru/C pH 4 | 100.00 | 4.34 | 8.77 |
| 5% Ru/C pH 4 | 100.00 | 0.39 | 2.28 |
| 1Na2WO4:2% Ru 0.1% S pH 4 | 100.00 | 1.24 | 4.55 |
| 2Na2WO4:2% Ru 0.1% S pH 4 | 100.00 | 1.19 | 2.46 |
| 3Na2WO4:2% Ru 0.1% S pH 4 | 100.00 | 0.89 | 1.46 |
| 4Na2WO4:2% Ru 0.1% S pH 4 | 100.00 | 1.19 | 1.99 |
| 5Na2WO4:2% Ru 0.1% S pH 4 | 100.00 | 1.16 | 1.66 |

The Reference for Table 11 is Johnson Matthey A3B00 Sponge Copper Batch 3B0000004.

The co-catalysts and processes using the co-catalysts in the present disclosure provides conversion of biomass or sugar feedstock and provides high propylene glycol yields and high propylene selectivity in a one-step process. The co-catalysts and processes using the co-catalysts allows for control of by-product formation, and reduces downstream costs incurred in conventional processes.

While the aspects described herein have been discussed with respect to specific examples including various modes of carrying out aspects of the disclosure, those skilled in the art will appreciate that there are numerous variations and permutations of the above described systems and techniques that fall within the spirit and scope of the invention.

The invention claimed is:

1. A process for directly converting a sugar feed comprised of fructose, dextrose or sucrose to a mixed lower polyols product including both propylene glycol and ethylene glycol, comprising supplying the sugar feed and a source of hydrogen to a reaction vessel and reacting the sugar feed and hydrogen in the presence of a hydrogenolysis catalyst comprising Mo and Ru to provide propylene glycol preferentially to ethylene glycol in the mixed lower polyols product.

2. The process of claim 1, wherein the Mo is present at 0.5 to 10% by weight of the sugar feed.

3. The process of claim 1 or claim 2, wherein the Ru is present at 3-7% by weight of the hydrogenolysis catalyst.

4. The process of claim 1, wherein the hydrogenolysis catalyst comprises a support material.

5. The process of claim 4, wherein the support material comprises carbon.

6. The process of claim 4, wherein the support material is selected from the group consisting of a carbon based support material, activated carbon, zirconium oxide, titanium oxide, niobium oxide, tin oxide, lanthanum oxide, tungsten oxide, silicon carbide, silicon oxycarbide, titanium carbide, titanium oxycarbide, zirconium oxycarbide, tungsten carbide, tungsten oxycarbide, and combination of any thereof.

7. The process of claim 6, wherein the Mo is present at about 9-10% by weight of the sugar feed.

8. The process of claim 7, wherein the Ru is present at about 5% by weight of the hydrogenolysis catalyst.

9. The process of claim 8, wherein the Mo is in the form of molybdate.

10. The process of claim 9, wherein the Mo is in the form of potassium molybdate.

11. The process of claim 10, wherein the Mo is in the form of potassium molybdate in the range of 3-10% by weight of the sugar feed.

12. The process of claim 1, wherein the sugar feed is placed in contact with the catalyst at a liquid hourly space velocity of between velocity of 0.2 $hr^{-1}$ to 2 $hr^{-1}$.

13. The process of claim 12, further comprising maintaining a reaction temperature of between 180 to 250 degrees C.

14. The process of claim 13, further comprising maintaining a hydrogen pressure of 600 to 2500 psi.

15. The process of claim 14, wherein the reaction vessel is a sealed hydrogenolysis reactor, and the process is conducted for a period of time in the range of 1 hour to 10 hours.

16. The process of claim 14, wherein the sugar feed is an aqueous fructose solution.

17. The process of claim 14, wherein the sugar feed is an aqueous sucrose solution.

18. The process of claim 14, wherein the sugar feed is an aqueous dextrose solution.

* * * * *